(12) United States Patent
Baril et al.

(10) Patent No.: US 11,622,790 B2
(45) Date of Patent: Apr. 11, 2023

(54) OBTURATORS FOR SURGICAL ACCESS ASSEMBLIES AND METHODS OF ASSEMBLY THEREOF

(71) Applicant: Covidien LP, Mansfield, MA (US)

(72) Inventors: Jacob C. Baril, Norwalk, CT (US); Garrett P. Ebersole, Hamden, CT (US); Justin J. Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 393 days.

(21) Appl. No.: 16/879,902

(22) Filed: May 21, 2020

(65) Prior Publication Data

US 2021/0361320 A1   Nov. 25, 2021

(51) Int. Cl.
*A61B 17/34*      (2006.01)

(52) U.S. Cl.
CPC .. *A61B 17/3423* (2013.01); *A61B 2017/3429* (2013.01)

(58) Field of Classification Search
CPC . A61B 17/34; A61B 17/3417; A61B 17/3423; A61B 10/04; A61B 2010/045
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |

(Continued)

FOREIGN PATENT DOCUMENTS

| | | |
|---|---|---|
| CA | 2702419 A1 | 11/2010 |
| EP | 0226026 A2 | 6/1987 |

(Continued)

*Primary Examiner* — Anu Ramana
(74) *Attorney, Agent, or Firm* — Carter, DeLuca & Farrell LLP

(57) ABSTRACT

An obturator includes a unitary body having an elongate portion, a handle portion formed on a proximal portion of the elongate portion, and a piercing tip formed on a distal portion of the elongate portion. The obturator further includes a section of heat shrink tubing received about the handle portion of the unitary body. A method of assembling an obturator includes selecting an obturator body having a unitary structure and having a handle portion, placing a section of heat shrink tubing about the handle portion of the obturator body, heating the section of heat shrink tubing to shrink the tubing about the handle portion, and trimming the section of heat shrink tubing.

19 Claims, 4 Drawing Sheets

(56) References Cited

U.S. PATENT DOCUMENTS

| | | |
|---|---|---|
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,263,937 A * | 11/1993 | Shipp ............... A61B 17/3417 606/167 |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,423,848 A * | 6/1995 | Washizuka ......... A61B 18/1487 604/164.11 |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,957,947 A * | 9/1999 | Wattiez ............... A61B 17/3417 606/185 |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A * | 8/2000 | Macoviak ............ A61M 25/06 604/173 |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,165,173 A * | 12/2000 | Kamdar ............ A61B 18/1206 606/41 |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 * | 5/2001 | Aboul-Hosn ...... A61B 17/3423 604/174 |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |

(56) References Cited

U.S. PATENT DOCUMENTS

| | | |
|---|---|---|
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Mbrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 * | 1/2011 | Butler ............... A61B 17/0293 600/208 |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 3,021,296 A1 | 9/2011 | Bonadio et al. |
| 3,025,670 A1 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |
| 8,480,683 B2 | 7/2013 | Fowler et al. |
| 8,574,153 B2 | 11/2013 | Richard |
| 8,585,632 B2 | 11/2013 | Okoniewski |
| 2001/0037053 A1 | 11/2001 | Bonadio et al. |

(56) References Cited

U.S. PATENT DOCUMENTS

| | | |
|---|---|---|
| 2002/0055714 A1 | 5/2002 | Rothschild |
| 2003/0014052 A1* | 1/2003 | Buysse .............. A61B 18/1445 |
| | | 606/208 |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0191714 A1* | 8/2007 | Cox ................ A61B 17/06061 |
| | | 128/898 |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |

(56) References Cited

U.S. PATENT DOCUMENTS

| | | | | |
|---|---|---|---|---|
| 2013/0296781 | A1* | 11/2013 | Tegg | A61M 25/0026 604/95.04 |
| 2013/0310651 | A1 | 11/2013 | Alfieri | |
| 2014/0018632 | A1 | 1/2014 | Kleyman | |

FOREIGN PATENT DOCUMENTS

| | | | |
|---|---|---|---|
| EP | 0538060 | A1 | 4/1993 |
| EP | 0577400 | A1 | 1/1994 |
| EP | 0630660 | A1 | 12/1994 |
| EP | 0807416 | A2 | 11/1997 |
| EP | 0950376 | A1 | 10/1999 |
| EP | 1188415 | A2 | 3/2002 |
| EP | 1312318 | A1 | 5/2003 |
| EP | 1774918 | A1 | 4/2007 |
| EP | 1932485 | A1 | 6/2008 |
| EP | 2044889 | A1 | 4/2009 |
| EP | 2044897 | A1 | 4/2009 |
| EP | 2080494 | A1 | 7/2009 |
| EP | 2095781 | A2 | 9/2009 |
| EP | 2098182 | A2 | 9/2009 |
| EP | 2138117 | A1 | 12/2009 |
| EP | 2138118 | A2 | 12/2009 |
| EP | 2181657 | A2 | 5/2010 |
| EP | 2226025 | A1 | 9/2010 |
| EP | 2229900 | A1 | 9/2010 |
| EP | 2238924 | A1 | 10/2010 |
| EP | 2238925 | A1 | 10/2010 |
| EP | 2238926 | A2 | 10/2010 |
| EP | 2238933 | A1 | 10/2010 |
| EP | 2248478 | A1 | 11/2010 |
| EP | 2248482 | A1 | 11/2010 |
| EP | 2253283 | A1 | 11/2010 |
| EP | 2272450 | A2 | 1/2011 |
| EP | 2277464 | A1 | 1/2011 |
| EP | 2289438 | A1 | 3/2011 |
| EP | 2292165 | | 3/2011 |
| EP | 2343019 | | 7/2011 |
| GB | 2469083 | | 4/2009 |
| WO | 8401512 | | 4/1984 |
| WO | 9314801 | | 8/1993 |
| WO | 9404067 | | 3/1994 |
| WO | 9610963 | | 4/1996 |
| WO | 9636283 | | 11/1996 |
| WO | 9733520 | | 9/1997 |
| WO | 9742889 | | 11/1997 |
| WO | 9916368 | | 4/1999 |
| WO | 9922804 | | 5/1999 |
| WO | 9929250 | | 6/1999 |
| WO | 0032116 | | 6/2000 |
| WO | 0032120 | | 6/2000 |
| WO | 0054675 | | 9/2000 |
| WO | 0108581 | | 2/2001 |
| WO | 0149363 | | 7/2001 |
| WO | 0207611 | | 1/2002 |
| WO | 03034908 | A2 | 5/2003 |
| WO | 03071926 | | 9/2003 |
| WO | 03077726 | | 9/2003 |
| WO | 2004043275 | | 5/2004 |
| WO | 2004054456 | | 7/2004 |
| WO | 2004075741 | | 9/2004 |
| WO | 2004075930 | | 9/2004 |
| WO | 2005058409 | | 6/2005 |
| WO | 2006019723 | | 2/2006 |
| WO | 2006100658 | A2 | 9/2006 |
| WO | 2006110733 | | 10/2006 |
| WO | 2007018458 | | 2/2007 |
| WO | 2007095703 | | 8/2007 |
| WO | 2007143200 | | 12/2007 |
| WO | 2008015566 | A2 | 2/2008 |
| WO | 2008042005 | | 4/2008 |
| WO | 2008077080 | | 6/2008 |
| WO | 2008093313 | | 8/2008 |
| WO | 2008103151 | | 8/2008 |
| WO | 2008121294 | A1 | 10/2008 |
| WO | 2008147644 | | 12/2008 |
| WO | 2009036343 | | 3/2009 |
| WO | 2010000047 | | 1/2010 |
| WO | 2010141409 | | 12/2010 |
| WO | 2010141673 | | 12/2010 |

\* cited by examiner

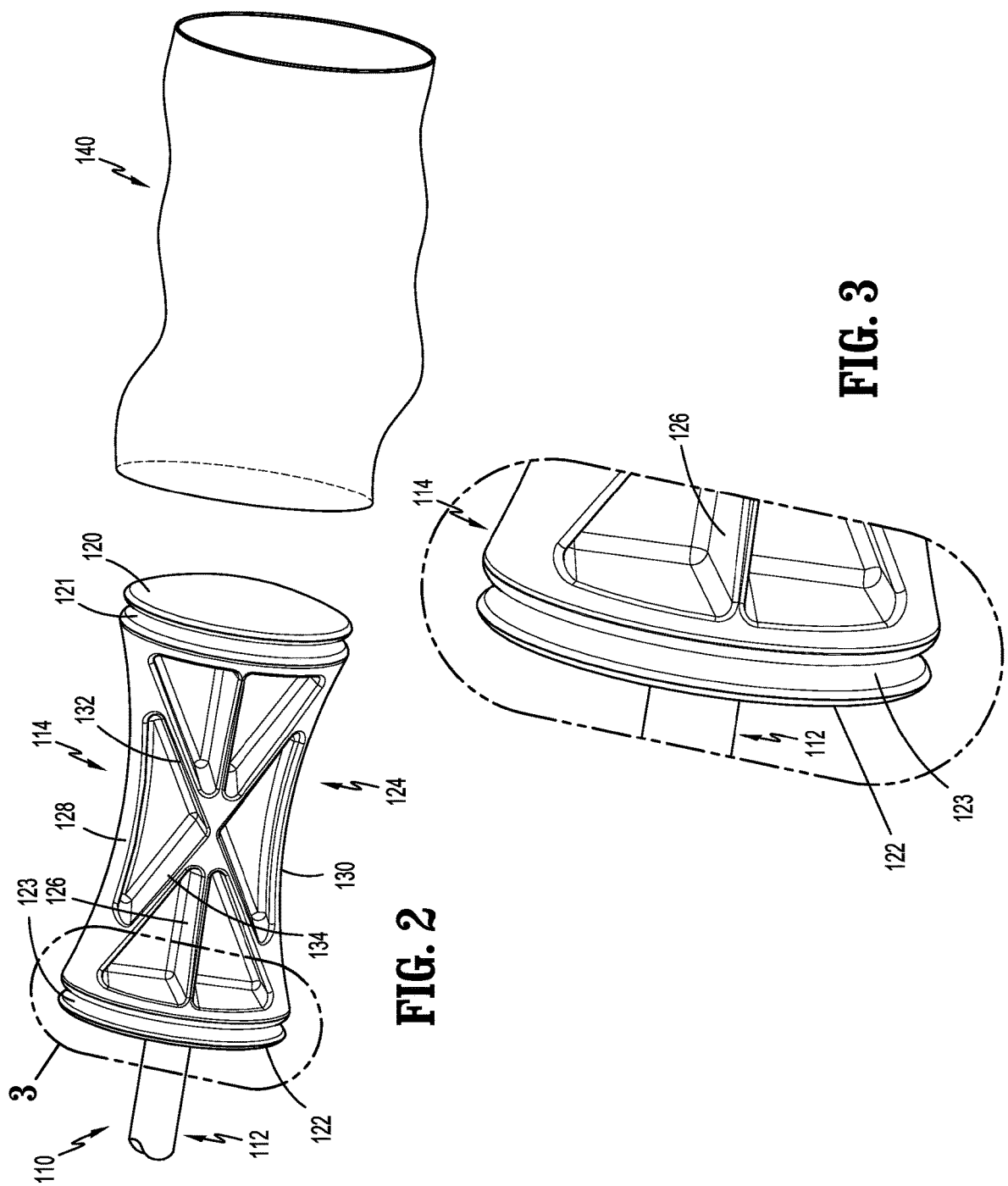

OBTURATORS FOR SURGICAL ACCESS ASSEMBLIES AND METHODS OF ASSEMBLY THEREOF

FIELD

The disclosure relates to access assemblies for minimally invasive surgery. More particularly, the disclosure relates to obturators for surgical access assemblies and methods of assembling the obturators.

BACKGROUND

Surgical access assemblies with obturators are employed during minimally invasive surgery, e.g., laparoscopic surgery, and provide for the sealed access of surgical instruments into an insufflated body cavity, such as the abdominal cavity. Insertion of the surgical access assemblies can be facilitated by an obturator. The obturator can have a blunt distal end, or a bladed or non-bladed penetrating distal end, and can be used to incise the abdominal wall so that the surgical access assembly can be introduced into the abdomen.

Many conventional obturators are manufactured in a costly two-step, overmolding process that requires large, and in many cases, complicated molds. It would be beneficial to have an obturator with a simplified and less costly method of manufacture.

SUMMARY

An obturator includes a unitary body having an elongate portion, a handle portion formed on a proximal portion of the elongate portion, and a piercing tip formed on a distal portion of the elongate portion. The obturator further includes a section of heat shrink tubing received about the handle portion of the unitary body.

In certain aspects of the disclosure, the handle portion includes proximal and distal disc portions and a frame structure extending between the proximal and distal disc portions. The frame structure may include a central support structure and first and second lateral support structures. The frame structure may further include first and second cross sections. The first and second cross sections may form an "X" shape. The proximal and distal disc portions may each define a groove. The piercing tip may include a cylindrical section having a conical distalmost end. The conical distalmost end of the cylindrical section may be configured to penetrate tissue. The elongate portion and piercing tip may be configured to be received through a 5 mm access assembly.

A method of assembling an obturator includes selecting an obturator body having a unitary structure and having a handle portion, placing a section of heat shrink tubing about the handle portion of the obturator body, heating the section of heat shrink tubing to shrink the tubing about the handle portion, and trimming the section of heat shrink tubing.

In certain aspects of the disclosure, placing the section of heat shrink tubing includes covering the handle portion with the section of heat shrink tubing. Placing the heat shrink tubing may include covering proximal and distal disc portions and a frame structure of the handle portion. Placing the heat shrink tubing may include covering a groove in each of the proximal and distal disc portions. Trimming the section of heat shrink tubing may include guiding a blade along the groove in each of the proximal and distal disc portions. Selecting the obturator body may include the obturator body having a piercing tip on a distal end of the elongate portion. At least one of placing the section of heat shrink tubing about the handle portion, heating the heat shrink tubing, and trimming the heat shrink tubing may be automated. Placing the section of heat shrink tubing about the handle portion, heating the heat shrink tubing, and trimming the heat shrink tubing may be automated.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the various aspects given below, serve to explain the principles of the disclosure, wherein:

FIG. 2 is a side perspective view of a handle assembly of the obturator shown in FIG. 1 including a handle portion of the obturator body and the section of heat shrink tubing prior to heating, with parts separated;

FIG. 3 is an enlarged view of the indicated area of detail of the handle portion of the obturator body shown in FIG. 2;

DETAILED DESCRIPTION

Figure 1:
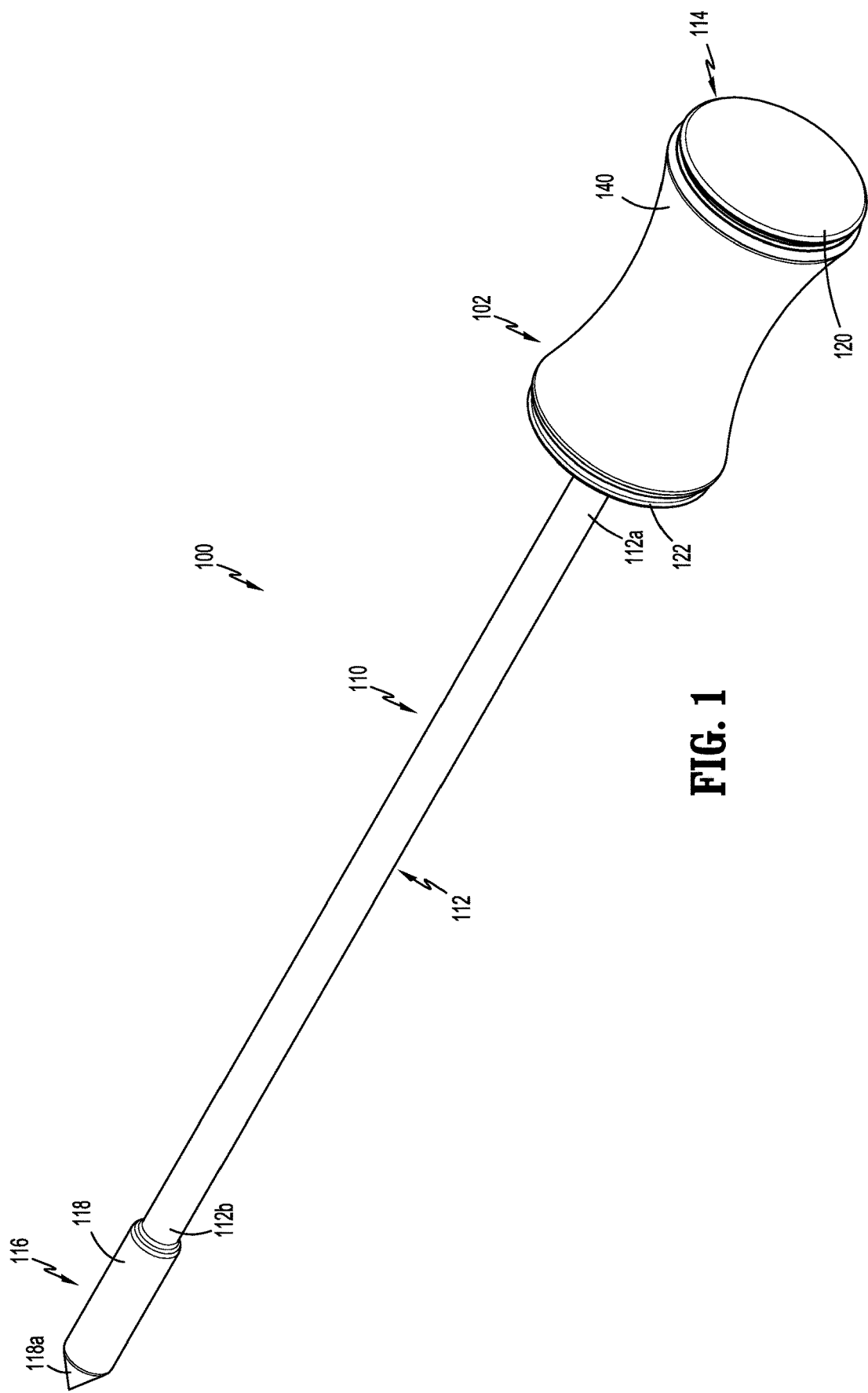
FIG. 1 is a side perspective view of an obturator according to an aspect of the disclosure including an obturator body and a section of heat shrink tubing.

The obturators and method of manufacturing the obturators of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. Like reference numerals refer to similar or identical elements throughout the description of the figures.

As used herein the term "distal" refers to that portion of the component farther from the user, while the term "proximal" refers to that portion of the component closer to the user. In addition, the term "clinician" is used generally to refer to medical personnel including doctors, nurses, and support personnel.

The obturators described below may be manufactured for use with access assemblies of varying size and structure. As will be described in further detail below, the method of manufacturing the obturators includes forming an obturator body and securing a single piece of heat shrink tubing about a handle portion of the obturator body. It is envisioned that this method of manufacturing will minimize part volume, simplify the mold, and/or reduce cycling time.

FIG. 1 illustrates an obturator according to aspects of the disclosure, shown generally as obturator 100. The obturator 100 includes an obturator body 110 and a section of heat shrink tubing 140 received about a proximal portion of the obturator body 110 to form a handle assembly 102. The obturator 100 may be formed in various sizes and configuration for use with a variety of access assemblies (not shown).

The obturator body 110 of the obturator 100 is formed of a single piece of molded plastic or other suitable material. The obturator body 110 includes an elongate portion 112 having a handle portion 114 formed on a proximal portion 112a of the elongate portion 112 and a piercing tip 116 formed on a distal portion 112b of the elongate portion 112. As will be described in further detail below, the handle portion 114 of the obturator body 110 is configured to receive the section of heat shrink tubing 140 and to facilitate operable engagement of the obturator 100 by a clinician during use.

As shown, the piercing tip 116 of the obturator body 110 includes a cylindrical portion 118 having a conical distalmost end 118a. The conical distalmost end 118a of the piercing tip 116 is configured to penetrate tissue (not shown). In certain aspects of the disclosure, the piercing tip 116 and the elongate portion 112 of the obturator body 110 are configured to be received through a 5 mm access assembly (not shown). It is envisioned that the piercing tip 116 may include alternative configurations. In other aspects of the disclosure, the piercing tip 116 may be configured to receive a blade (not shown).

FIG. 2 illustrates the handle portion 114 of the obturator body 110 of the obturator 100 and the section of heat shrink tubing 140. The handle portion 114 includes proximal and distal disc portions 120, 122, and a frame structure 124 extending between the proximal and distal disc portions 120, 122. The frame structure 124 is configured to provide strength to the handle assembly 102 while reducing the amount of material needed to form the handle assembly 102. The length of the handle portion 114 may be varied to accommodate a clinician's preferences.

The frame structure 124 of the handle portion 114 of the obturator body 110 includes a central support section 126 and first and second lateral support sections 128, 130 spaced from the central support section 126. The first and second lateral support sections 128, 130 may be curved, as shown, and/or be otherwise configured, e.g., with knurling, ridges, and/or grooves, to facilitate operable engagement of the handle assembly 102 by a clinician.

First and second cross sections 132, 134 extend between the first and second lateral support sections 128, 130. The first and second cross sections 132, 134 form an "X" configuration and are configured to strengthen the integrity of the frame structure 124.

FIG. 3 illustrates the distal disc portion 122 of the handle portion 114 of the obturator body 110. The distal disc portion 122 defines a groove 123 formed in an outer circumference of the distal disc portion 122. Similarly, the proximal disc portion 120 defines a groove 121 formed in an outer circumference of the proximal disc portion 120. As will be described in further detail below, the grooves 121, 123 in the respective proximal and distal disc portions 120, 122 facilitate trimming of the section of heat shrink tubing 140 during manufacturing of the obturator 100 and allow for sharp, crisp edges of the trimmed section of heat shrink tubing 140.

The method of assembling the obturator 100 will now be described with reference to FIGS. 4-7. Initially, the obturator body 110 is formed as a single, unitary structure, e.g., monolithic, using any suitable forming process. In certain aspects of the disclosure, the obturator body 110 is formed by a molding process, it is envisioned that the obturator body 110 may be formed through a milling process or a 3-D printing process. It is further envisioned that the handle portion 114 of the obturator body 110 may be formed with one or more engagement structures (not shown) configured for releasably engaging an access assembly (not shown).

Figure 4:
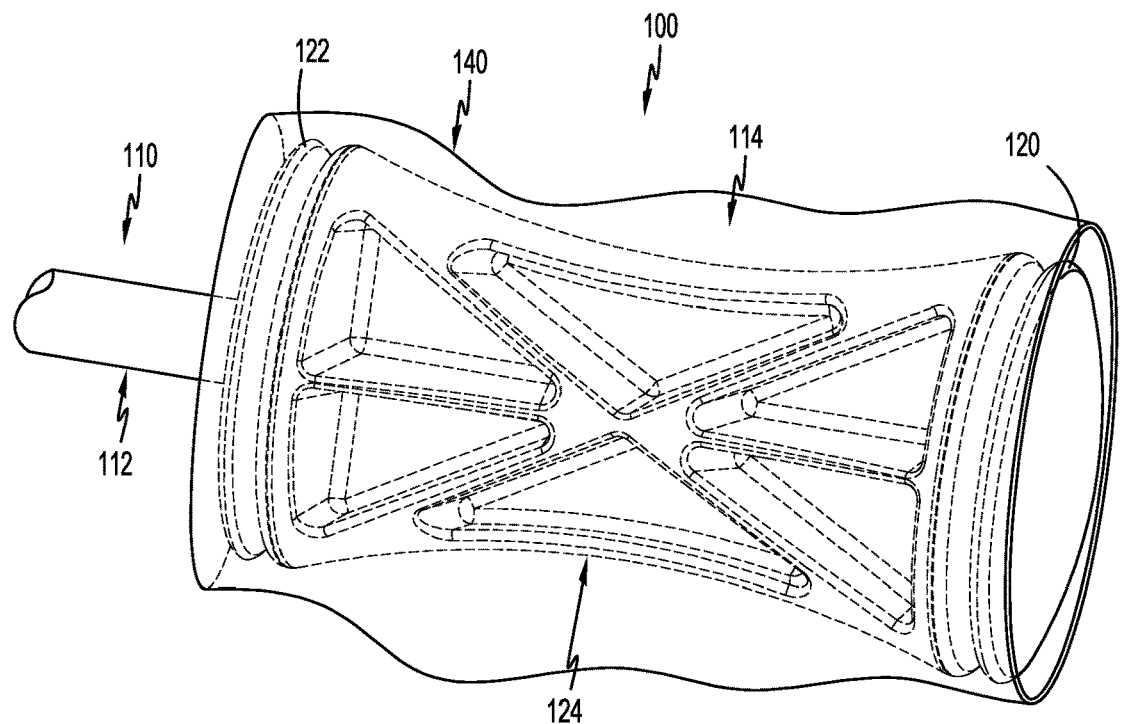
FIG. 4 is a side perspective view of the handle assembly shown in FIG. 2 subsequent to receiving the section of heat shrink tubing about the handle portion and prior to heating the section of heat shrink tubing.

FIG. 4 illustrates handle portion 114 of the obturator body 110 subsequent to the section of heat shrink tubing 140 being received over the handle portion 114 of the obturator body 110 and prior to the heat shrink tubing 140 being heated. Prior to heating, the section of heat shrink tubing 140 easily slides over the handle portion 114 as an inner diameter of the section of the heat shrink tubing 140 is greater than an outer diameter of the handle portion 114. When received over the handle portion 114, the section of heat shrink tubing 140 extends beyond the proximal and distal disc portions 120, 122 of the handle portion 114.

Figure 5:
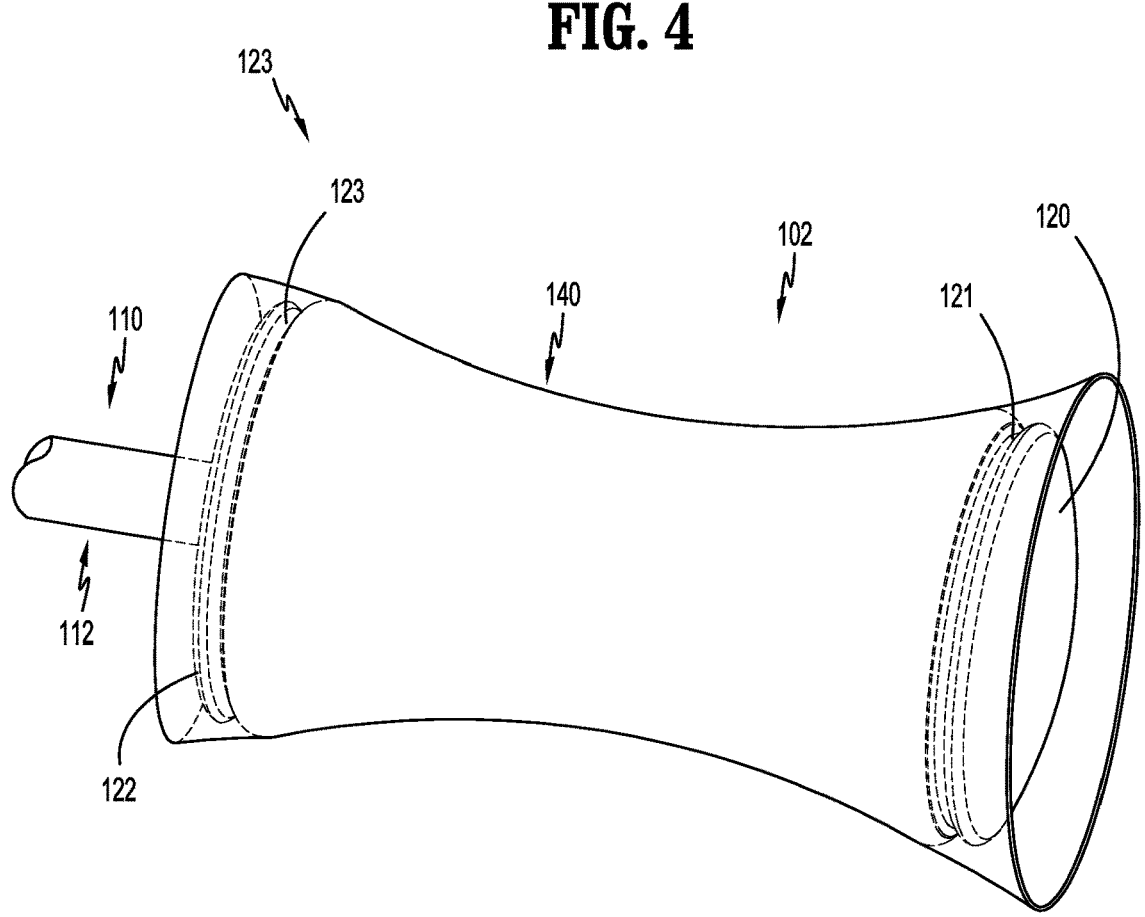
FIG. 5 is a side perspective view of the handle assembly shown in FIG. 4, subsequent to the section of heat shrink tubing being heated.

FIG. 5 illustrates the handle portion 114 of the obturator body 110 and the heat shrink tubing 140 subsequent to heating of the section of heat shrink tubing 140, i.e., after the section of heat shrink tubing 140 has been heated. Heating of the section of heat shrink tubing 140 causes the section of heat shrink tubing 140 to contract, or shrink, about the handle portion 114 and conform to the handle portion 114. It is envisioned that heating of the section of heat shrink tubing 140 may be accomplished in an oven, with a hot air gun, or in any other suitable manner, manually or in an automated process. Prior to trimming the section of heat shrink tubing 140, the section of heat shrink tubing 140 extends beyond the proximal and distal disc portions 120, 122.

Figure 6:
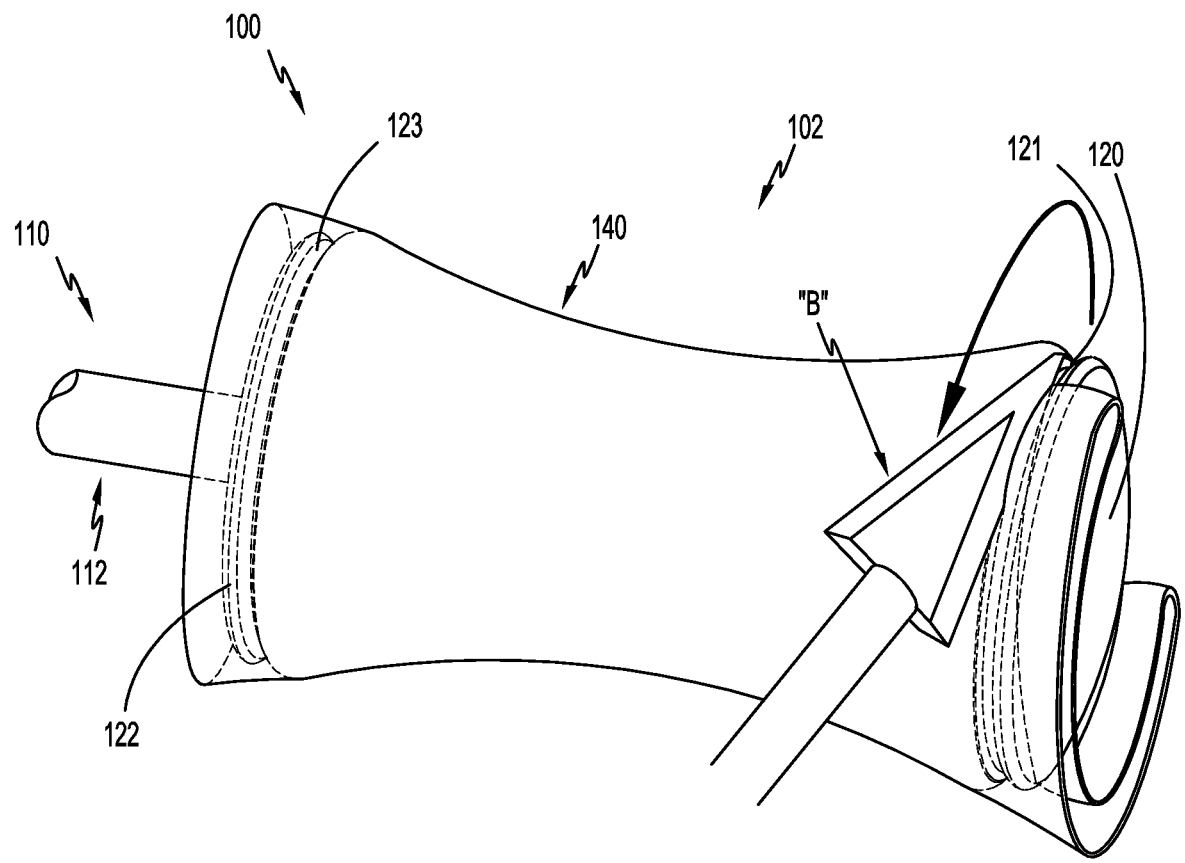
FIG. 6 is a side perspective view of the handle assembly shown in FIG. 5 as the section of heat shrink tubing is trimmed.

FIG. 6 illustrates trimming of the section of heat shrink tubing 140 subsequent to the section of heat shrink tubing 140 being heated. The grooves 121, 123 in the respective proximal and distal disc portions 120, 122 of the handle portion 114 of the obturator body provide a guide for facilitating trimming of the section of heat shrink tubing 140. As noted above, the grooves 121, 123 allow for sharp, crisp edges to the section of heat shrink tubing 140. The heat shrink tubing 140 may be trimmed using a blade "B" or other suitable means, in a manual or automated process. The excess portions of the section of heat shrink tubing 140 are discarded.

Figure 7:
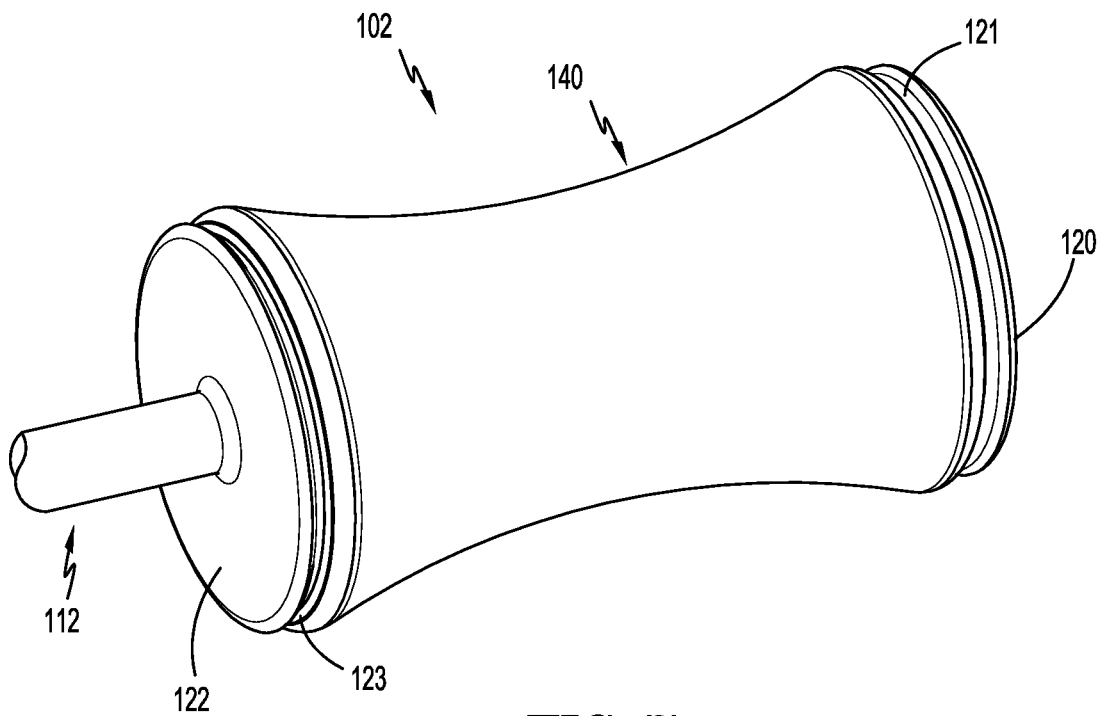
FIG. 7 is a side perspective view of handle assembly shown in FIG. 5, subsequent to the heat shrink tubing being trimmed.

FIG. 7 illustrates the completed handle assembly 102 of the obturator 100 with the section of heat shrink tubing 140 trimmed to fit the handle portion 114 of the handle assembly 102.

It is envisioned that any or all of the manufacturing of the obturator 100 may be performed manually or in in automated process.

Persons skilled in the art will understand that the devices and methods specifically described herein and illustrated in the accompanying drawings are non-limiting and exemplary. It is envisioned that the elements and features illustrated or described in connection with one aspect of the disclosure may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

The invention claimed is:

1. An obturator comprising:
   a unitary body having:
   an elongate portion;
   a handle portion formed on a proximal portion of the elongate portion, the handle portion including a proximal disc portion and a distal disc portion, each of the proximal disc portion and the distal disc portion defining a groove; and
   a piercing tip formed on a distal portion of the elongate portion; and
   a section of heat shrink tubing received about the handle portion of the unitary body.

2. The obturator of claim 1, wherein the handle portion further includes a frame structure extending between the proximal disc portion and the distal disc portion.

3. The obturator of claim 2, wherein the frame structure includes a central support structure a first lateral support structure, and a second lateral support structure.

4. The obturator of claim 3, wherein the frame structure further includes a first cross section and a second cross section.

5. The obturator of claim 4, wherein the first cross section and the second cross section form an "X" shape.

6. The access assembly of claim 1, wherein the piercing tip includes a cylindrical section having a conical distalmost end.

7. The obturator of claim 6, wherein the conical distalmost end of the cylindrical section is configured to penetrate tissue.

8. The obturator of claim 1, wherein the elongate portion and piercing tip are configured to be received through a 5 mm access assembly.

9. A method of assembling an obturator, the method comprising:
   selecting an obturator body having a unitary structure and having a handle portion;
   placing a section of heat shrink tubing about the handle portion of the obturator body, the handle portion including a proximal disc portion and a distal disc portion, the heat shrink tubing covering a groove in the proximal disc portion and a groove in the distal disc portion;
   heating the section of heat shrink tubing to shrink the tubing about the handle portion; and
   trimming the section of heat shrink tubing.

10. The method of claim 9, wherein placing the section of heat shrink tubing includes covering the handle portion with the section of heat shrink tubing.

11. The method of claim 9, wherein placing the heat shrink tubing includes covering a frame structure of the handle portion.

12. The method of claim 11, wherein selecting the obturator body includes the obturator body having a piercing tip on a distal end of the elongate portion.

13. The method of claim 9, wherein trimming the section of heat shrink tubing includes guiding a blade along the groove in each of the proximal disc portion and the distal disc portion.

14. An obturator comprising:
   a unitary body having:
   an elongate portion;
   a handle portion formed on a proximal portion of the elongate portion, the handle including a proximal disc portion, a distal disc portion, and a frame structure extending between the proximal disc portion and the distal disc portion, the frame structure including a central support structure, a first lateral support structure, and a second lateral support structure; and
   a piercing tip formed on a distal portion of the elongate portion; and
   a section of heat shrink tubing disposed about the handle portion.

15. The obturator of claim 14, wherein the frame structure further includes a first cross section and a second cross section.

16. The obturator of claim 15, wherein in the first cross section and the second cross section form an "X" shape.

17. The obturator of claim 14, wherein each of the proximal disc portion and the distal disc portion defines a groove.

18. The obturator of claim 14, wherein the piercing tip includes a cylindrical section having a conical distalmost end.

19. The obturator of claim 14, wherein the elongate portion and piercing tip are configured to be received through a 5 mm access assembly.

* * * * *